(12) United States Patent
Toda et al.

(10) Patent No.: US 11,386,688 B2
(45) Date of Patent: Jul. 12, 2022

(54) IMAGING DEVICE

(71) Applicant: SONY SEMICONDUCTOR SOLUTIONS CORPORATION, Kanagawa (JP)

(72) Inventors: Atsushi Toda, Kanagawa (JP); Koji Furumi, Tokyo (JP)

(73) Assignee: SONY SEMICONDUCTOR SOLUTIONS CORPORATION, Kanagawa (JP)

( * ) Notice: Subject to any disclaimer, the term of this patent is extended or adjusted under 35 U.S.C. 154(b) by 546 days.

(21) Appl. No.: 16/325,086

(22) PCT Filed: May 24, 2017

(86) PCT No.: PCT/JP2017/019356
§ 371 (c)(1),
(2) Date: Feb. 12, 2019

(87) PCT Pub. No.: WO2018/042778
PCT Pub. Date: Mar. 8, 2018

(65) Prior Publication Data
US 2021/0286968 A1    Sep. 16, 2021

(30) Foreign Application Priority Data
Aug. 29, 2016  (JP) .............................. JP2016-166794

(51) Int. Cl.
*G06V 40/13* (2022.01)
*G06V 40/12* (2022.01)

(52) U.S. Cl.
CPC .......... *G06V 40/13* (2022.01); *G06V 40/1376* (2022.01)

(58) Field of Classification Search
CPC .............................. G06K 9/0004; G06F 3/042
See application file for complete search history.

(56) References Cited

U.S. PATENT DOCUMENTS 9,213,438 B2 * 12/2015 Su .......................... G06F 3/042
2009/0076322 A1   3/2009 Matsunaga et al.
(Continued)

FOREIGN PATENT DOCUMENTS

CN      101485570 A    7/2009
JP    2008-071137 A    3/2008
(Continued)

OTHER PUBLICATIONS

International Search Report and Written Opinion of PCT Application No. PCT/JP2017/019356, dated Jun. 27, 2017, 10 pages of ISRWO.
(Continued)

*Primary Examiner* — Joseph R Haley
(74) *Attorney, Agent, or Firm* — Chip Law Group

(57) ABSTRACT

Provided is an imaging device including a light source that radiates light in at least two different wavelength bands and an imaging element that acquires signals individually from the light in the two different wavelength bands. The two different wavelength bands include a first wavelength band from 400 to 580 nm for use in dermatoglyphic pattern authentication, and a second wavelength band of 650 nm or more mainly including near-infrared rays for use in vein authentication.

13 Claims, 10 Drawing Sheets

(56) References Cited

U.S. PATENT DOCUMENTS

| | | | |
|---|---|---|---|
| 2009/0152664 A1* | 6/2009 | Klem | H01L 27/14641 257/440 |
| 2009/0214083 A1 | 8/2009 | Sato | |
| 2011/0013074 A1* | 1/2011 | Ichimura | G06K 9/0004 348/360 |
| 2017/0124376 A1* | 5/2017 | Wyrwas | G06K 9/2018 |
| 2017/0220844 A1* | 8/2017 | Jones | G06F 3/0421 |
| 2017/0277934 A1* | 9/2017 | Hama | G06K 9/0004 |

FOREIGN PATENT DOCUMENTS

| | | |
|---|---|---|
| JP | 2008-198083 A | 8/2008 |
| JP | 2009-089351 A | 4/2009 |
| JP | 2009-165630 A | 7/2009 |
| JP | 2009-276976 A | 11/2009 |
| JP | 2010-039659 A | 2/2010 |
| JP | 2010-134685 A | 6/2010 |
| WO | 2012/005163 A1 | 1/2012 |
| WO | 2014/115682 A1 | 7/2014 |
| WO | 2016/098283 A1 | 6/2016 |

OTHER PUBLICATIONS

Aihara, et al., "Stacked Color Image Sensor Using Wavelength-Selective Organic Photoconductive Films With Zinc-Oxide Thin Film Transistors As Signal Readout Circuit", Proceedings of SPIE—The International Society for Optical Engineering.

Fujieda, et al., "Fingerprint Input Based on Scattered-Light Detection", Applied Optics, vol. 36, No. 35, Dec. 10, 1997, pp. 9152-9156.

Fujieda et al., "Fingerprint Input Based on Scattered-Light Detection", Applied Optics, vol. 36, Issue 35, Dec. 10, 1997, 5 pages.

* cited by examiner

IMAGING DEVICE

CROSS REFERENCE TO RELATED APPLICATIONS

This application is a U.S. National Phase of International Patent Application No PCT/JP2017/019356 filed on May 24, 2017, which claims priority benefit of Japanese Patent Application No. JP 2016-166794 filed in the Japan Patent Office on Aug. 29, 2016. Each of the above-referenced applications is hereby incorporated herein by reference in its entirety.

TECHNICAL FIELD

The present disclosure relates to an imaging device.

BACKGROUND ART

In recent years, biometric authentication techniques using human physical features for personal authentication have been widespread. For example, Non-Patent Literature 1 discloses a fingerprint authentication technique using scattered light. In addition, there have recently been developed devices that acquire a plurality of physical features and perform biometric authentication on the basis of the plurality of physical features. For example, Patent Literature 1 discloses a personal identification device that acquires fingerprint data and vein data, corrects displacements of the fingerprint data on the basis of the vein data, and performs biometric authentication using the corrected fingerprint data.

CITATION LIST

Patent Literature

Patent Literature 1: JP 2008-198083A

Non-Patent Literature

Non-Patent Literature 1: Ichiro Fujieda and Hiroshi Haga, "Fingerprint input based on scattered-light detection", APPLIED OPTICS, Vol. 36, No. 35, 1997

DISCLOSURE OF INVENTION

Technical Problem

However, the technique disclosed in Non-Patent Literature 1 is a technique for effectively acquiring the unevenness on the surface of an object. Therefore, in case where fingertips and fingerprints are forged using a material, such as silicone, there is a possibility that the forgery is overlooked in the technique disclosed in Non-Patent Literature 1.

Furthermore, the personal identification device disclosed in Patent Literature 1 acquires fingerprint data and vein data by using the transmittance pattern of light radiated from light sources. For this, the light sources need to be disposed opposite an imaging unit across the finger in the personal identification device disclosed in Patent Literature 1. This configuration makes it difficult to downsize the device.

In such a circumstance, the present disclosure proposes a novel and improved imaging device having a compact housing and capable of acquiring a plurality of physical features for use in biometric authentication.

Solution to Problem

According to the present disclosure, there is provided an imaging device including: a light source configured to radiate light in at least two different wavelength bands; and an imaging element configured to acquire signals individually from the light in two different wavelength bands. The two different wavelength bands include a first wavelength band from 400 to 580 nm for use in dermatoglyphic pattern authentication, and a second wavelength band of 650 nm or more mainly including near-infrared rays for use in vein authentication.

Advantageous Effects of Invention

According to the present disclosure as described above, it is possible to acquire a plurality of physical features for use in biometric authentication with a compact housing.

Note that the effects described above are not necessarily limitative. With or in the place of the above effects, there may be achieved any one of the effects described in this specification or other effects that may be grasped from this specification.

MODES FOR CARRYING OUT THE INVENTION

Figure 1:
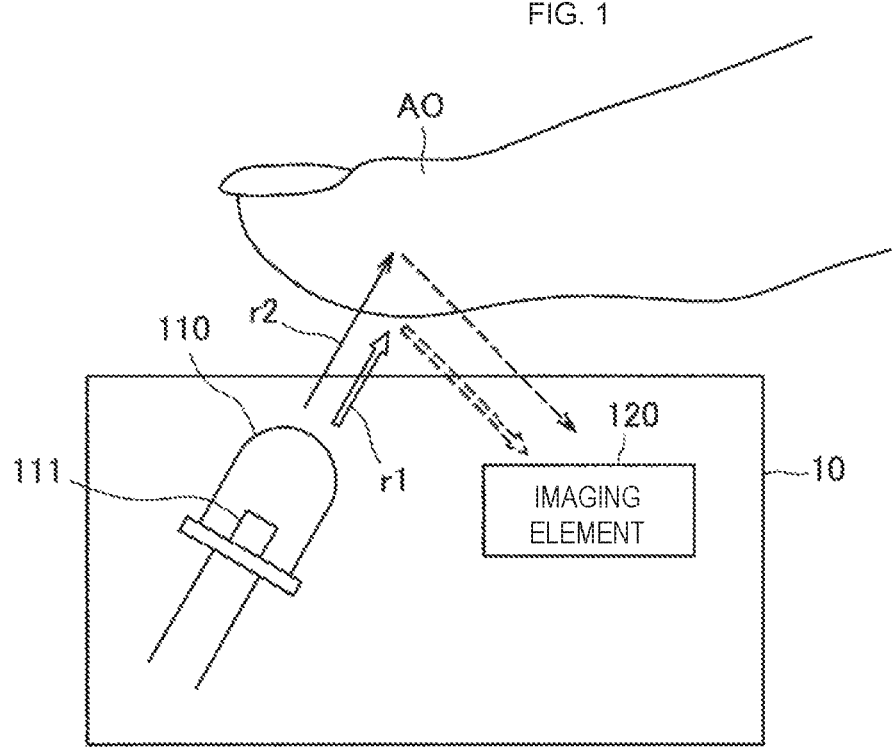
FIG. 1 is a view for describing an overview of biometric authentication using an imaging device according to a first embodiment of the present disclosure.

Hereinafter, (a) preferred embodiment(s) of the present disclosure will be described in detail with reference to the appended drawings. Note that, in this specification and the appended drawings, structural elements that have substantially the same function and structure are denoted with the same reference numerals, and repeated explanation of these structural elements is omitted.

Note that description will be given in the following order.
1. Introduction
   1.1. Overview of Imaging Device according to Present Disclosure
2. First Embodiment
   2.1. Structure of Imaging Device 10 According to First Embodiment
   2.2. Light Source 110 According to First Embodiment
   2.3. Imaging Element 120 According to First Embodiment
3. Second Embodiment
   3.1. Light Source 110 According to Second Embodiment
4. Third Embodiment
   4.1. Imaging Element 120 According to Third Embodiment
5. Fourth Embodiment
   5.1. Imaging Element 120 According to Fourth Embodiment
6. Fifth Embodiment
   6.1. Imaging Element 120 According to Fifth Embodiment
7. Sixth Embodiment
   7.1. Proximity Imaging Device 10 According to Sixth Embodiment
8. Seventh Embodiment
   8.1. Image Forming Lens-Type Imaging Device 10 According to Seventh Embodiment
9. Conclusion

1. Introduction (1.1. Overview of Imaging Device According to Present Disclosure)

First, an overview of a first embodiment according to the present disclosure will be described. As described above, techniques of identifying persons through biometric authentication using human physical features have recently been widespread. In particular, fingerprint authentication for personal identification through comparison between the captured fingerprint and the stored personal data has been employed in many devices and widely commercialized.

However, since the fingerprint authentication as described above uses the captured uneven pattern on the finger surface for identification, there is a possibility that the forged uneven pattern if made by using a material, such as silicone, is overlooked. It is thus difficult to ensure adequate security of devices that identify persons through general fingerprint authentication.

An imaging device according to the present disclosure has been conceived by focusing on the above-described point. The imaging device can capture the dermatoglyphic pattern on the skin surface and the vein pattern under the skin simultaneously or with a time lag.

Therefore, the imaging device according to the present disclosure uses light in two different wavelength bands to capture the dermatoglyphic pattern and the vein pattern. More specifically, the imaging device according to the present disclosure has a function of radiating light in a first wavelength band from 400 to 580 nm for use in dermatoglyphic pattern authentication, and light in a second wavelength band of 650 nm or more mainly including near-infrared rays for use in vein authentication. In addition, the imaging device according to the present disclosure has a function of acquiring signals individually from the light in two different wavelength bands reflected off an authentication target object.

The above-described functions of the imaging device according to the present disclosure enable biometric authentication using both dermatoglyphic pattern authentication and vein authentication, which eliminates the possibility of overlooking forged fingerprints to realize secure biometric authentication. Furthermore, the housing of an imaging device can be downsized due to imaging based on the light reflected from the authentication target object. In the following description of the embodiments, the structural features of the imaging device according to the present disclosure and the advantage effects of the features will be described in detail.

2. First Embodiment (2.1. Structure of Imaging Device 10 According to First Embodiment)

Next, a first embodiment of the present disclosure will be described. FIG. 1 is a view for describing an overview of biometric authentication using an imaging device 10 according to this embodiment. FIG. 1 illustrates an authentication target object AO and an imaging device 10 according to this embodiment. Here, FIG. 1 illustrates the case where the authentication target object AO is a human finger. In other words, the example illustrated in FIG. 1 is a case where the imaging device 10 according to this embodiment captures the fingerprint pattern on the finger surface and the vein pattern of the fingertip.

However, the authentication target object AO according to this embodiment is not limited to the example illustrated in FIG. 1. The authentication target object according to this embodiment may be, for example, the palm. In the case where the authentication target object is the palm, the imaging device 10 according to this embodiment can capture the palmprint pattern on the palm surface and the vein pattern of the palm. Thus, the dermatoglyphic pattern according to this embodiment may contain various patterns on the skin surface, such as fingerprints and palmprints.

Referring to FIG. 1, the imaging device 10 according to this embodiment includes a light source 110 and an imaging element 120. In addition, the light source 110 according to this embodiment includes a light emitting unit 111. Here, the light emitting unit 111 has a function of radiating the light in the first wavelength band and the light in the second wavelength band. FIG. 1 illustrates how the light emitting unit 111 radiates the light r1 in the first wavelength band and the light r2 in the second wavelength band.

Here, the light r1 in the first wavelength band may be light from 400 to 580 nm for use in dermatoglyphic pattern authentication. For example, as described in Non-Patent Literature 1, it is generally known that the scattering coefficient of the skin surface and the molar absorptivity of the melanin pigment depend on the wavelength of light. Specifically, the scattering coefficient and the molar absorptivity tend to be lower at longer wavelengths. For this, light having a longer wavelength is less subject to scattering or absorption and thus penetrates the skin. In other words, in the case where long wavelength light is used to capture the dermatoglyphic pattern, the light that has penetrated the skin reflects off the tissues under the skin and becomes background light during imaging, which may cause resolution deterioration. For this reason, short wavelength light is effectively used to capture the dermatoglyphic pattern.

On the basis of the foregoing description, a dermatoglyphic pattern with high resolution can be obtained by using light from 400 to 580 nm mainly including blue to green visible light for imaging in this embodiment. Note that ultraviolet rays can be used from the viewpoint of resolution, but ultraviolet rays may damage the skin. For this reason, the effect on the skin can be reduced by mainly using blue to green visible light in this embodiment.

In addition, the light r2 in the second wavelength band may be light of 650 nm or more mainly including near-infrared rays for use in vein authentication. In general, veins are blood vessels present at a depth of ~2 mm from the skin surface. It is thus difficult for short wavelength light to penetrate the skin due to the effect of diffusion and absorption described above. In this embodiment, the vein pattern can be captured by using light of 650 nm or more mainly including near-infrared rays.

Figure 2:
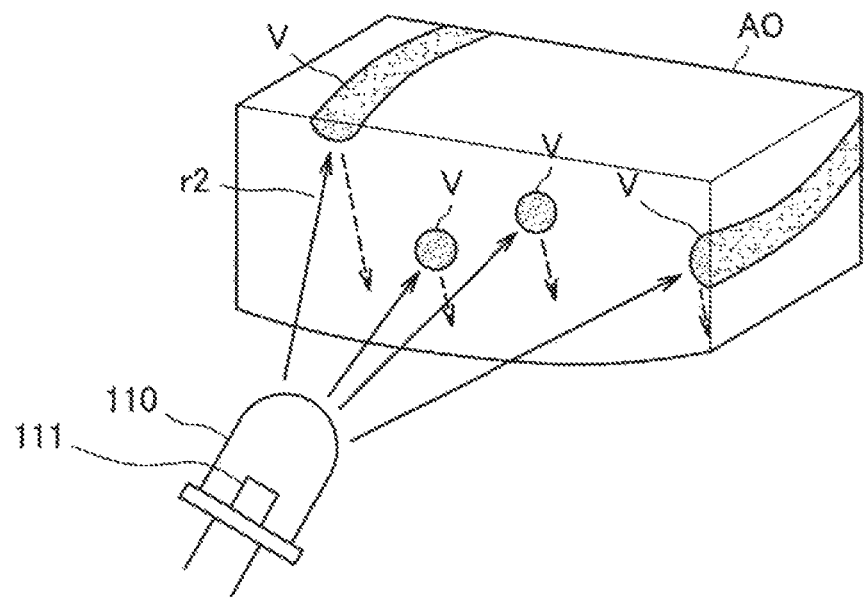
FIG. 2 is a view for describing capturing of a vein pattern according to this embodiment.

FIG. 2 is a view for describing capturing of the vein pattern according to this embodiment. FIG. 2 illustrates a conceptual diagram of the internal configuration of the authentication target object AO and the light source 110 according to this embodiment. As illustrated in FIG. 2, the light r2 in the second wavelength band radiated from the light source 110 enters the authentication target object AO and reflects off the veins V.

Returning to FIG. 1, description will be continued. As described above, the light emitting unit 111 according to this embodiment can radiate the light r1 in the first wavelength band effective for capturing the dermatoglyphic pattern and the light r2 in the second wavelength band effective for capturing the vein pattern. In addition, as illustrated in FIG. 1, the light r1 in the first wavelength band reflects off the skin surface of the authentication target object AO, and the light r2 in the second wavelength band reflects under the skin of the authentication target object AO.

In the example illustrated in FIG. 1, the light r1 in the first wavelength band and the light r2 in the second wavelength band radiated from the light emitting unit 111 are indicated by straight arrows, and the light beams reflected off the authentication target object AO are indicated by dotted arrows. Similarly, the straight arrows in the figures of the present disclosure indicate the light r1 in the first wavelength band or the light r2 in the second wavelength band radiated from the light emitting unit 111, and the dotted arrows indicate the light reflected from the authentication target object AO in the following description.

Subsequently, an overview of the imaging element 120 according to this embodiment will be described. The imaging element 120 according to this embodiment has a function of acquiring signals individually from light in two different wavelength bands. In other words, the imaging element 120 according to this embodiment can acquire signals separately from the light r1 in the first wavelength band and the light r2 in the second wavelength band. When the light emitting unit 111 according to this embodiment radiates light in two different wavelength bands in this manner and the imaging element 120 acquires signals individually from the light in two different wavelength bands, the dermatoglyphic pattern and the vein pattern can be captured simultaneously.

In addition, the imaging element according to this embodiment acquires signals from light radiated from the light emitting unit 111 and reflected off the authentication target object AO. In other words, the light source 110 and the imaging element 120 according to this embodiment may be disposed on the same side with respect to the authentication target object AO.

Since the personal identification device disclosed in Patent Literature 1 performs authentication using the transmittance pattern of light radiated from the light sources as described above, the light sources need to be disposed opposite the imaging unit across an authentication target object. However, since the imaging element 120 according to this embodiment performs imaging based on the light reflected from the authentication target object AO, the light source 110 and the imaging element 120 can be disposed on the same side with respect to the authentication target object AO. This configuration makes it possible to downsize the housing of the imaging device 10. For this, for example, the imaging device 10 according to this embodiment can also be used in information processing terminals, such as smartphones, tablets, and personal computers (PCs).

The example structure of the imaging device 10 according to this embodiment is described above. In the foregoing description, the case where the imaging device 10 includes the light source 110 and the imaging element 120 is illustrated as an example. The structure of the imaging device 10 according to this embodiment is not limited to this example. The imaging device according to this embodiment may further include components other than those illustrated in FIG. 1. The imaging device according to this embodiment may further include, for example, a storage unit configured to store the dermatoglyphic pattern and the vein pattern for each person, an authentication unit configured to perform personal authentication through comparison of the captured image with the stored data. The structure of the imaging device 10 according to this embodiment can freely be changed in accordance with specifications, operations, and the like.

(2.2. Light Source 110 According to First Embodiment)

Figure 3:
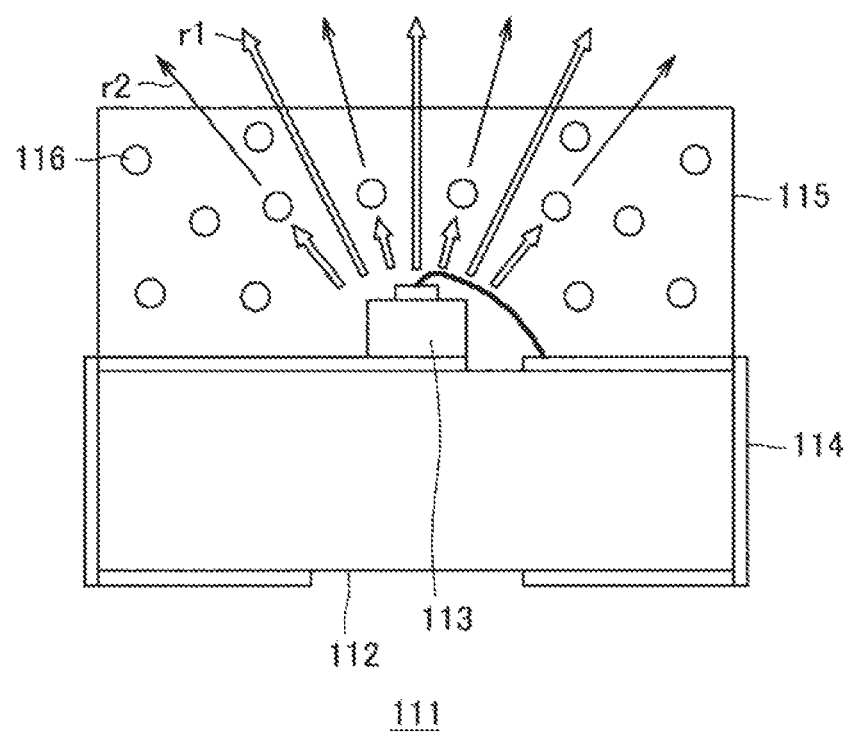
FIG. 3 is a view illustrating the structure of a light emitting unit according to this embodiment.

Next, the light source 110 according to the first embodiment of the present disclosure will be described in detail. As described above, the light source 110 according to this embodiment has a function of radiating the light r1 in the first wavelength band effective for capturing the dermatoglyphic pattern and the light r2 in the second wavelength band effective for capturing the vein pattern. Hereinafter, the structure of the light source 110 for realizing this function will be described in detail. FIG. 3 is a view illustrating the structure of the light emitting unit 111 according to this embodiment. The light source 110 according to this embodiment may include at least one or more light emitting units 111 as illustrated in FIG. 3.

Referring to FIG. 3, the light emitting unit 111 according to this embodiment includes a substrate 112, a light emitting element 113, an electrode 114, and a transparent material 115. In addition, a plurality of light emitting substances 116 is enclosed in the transparent material 115.

Here, the substrate 112 functions as a base on which the light emitting element 113, the electrode 114, and the transparent material 115 are disposed.

In addition, the light emitting element 113 may be realized by a light emitting diode (LED), electro-luminescence (EL), or the like, which radiates the light r1 in the first wavelength band from 400 to 580 nm. For example, a material, such as a GaInN-based material, a ZnMgCdSe-based material, and a ZnInO-based material, may be used for the light emitting element 113 according to this embodiment.

Furthermore, the electrode 114 has a function of supplying electric power for causing the light emitting element 113 to emit light. The electrode 114 may be formed by an anode, a cathode, or the like.

In addition, the transparent material 115 is a material in which the light emitting substance 116 is enclosed. For example, a material, such as transparent resin or glass, may be used as the transparent material 115 according to this embodiment.

The light emitting substance 116 emits the light r2 in the second wavelength band of 650 nm or more mainly including near-infrared rays upon being excited by light emitted from the light emitting element 113. The light emitting substance 116 according to this embodiment can be realized by a near-infrared phosphor, a phosphorescent material, a quantum dot, or the like having this feature. For example, a phosphor, such as ZnS, having a rare earth ion $Yb^{3+}$, $Tm^{3+}$, $Nd^{3+}$ or the like at a light emission center, may be used as the light emitting substance 116 according to this embodiment. For example, a quantum dot containing GaAs, InGaAs, or the like can also be used as the light emitting substance 116 according to this embodiment.

The structure of the light emitting unit 111 according to this embodiment is described above. As described above, the light emitting unit 111 according to this embodiment includes the light emitting element 113, which is configured to radiate the light r1 in the first wavelength band from 400 to 580 nm. In addition, the light emitting unit 111 according to this embodiment includes the light emitting substance 116, which emits the light r2 in the second wavelength band of 650 nm or more mainly including near-infrared rays upon being excited by light emitted from the light emitting element 113.

In other words, at least one or more light emitting units 111 as described above in the light source 110 according to this embodiment enables simultaneous radiation of light in the first wavelength band and light in the second wavelength band. Therefore, the light source 110 according to this embodiment enables the imaging element 120 to capture the dermatoglyphic pattern and the vein pattern simultaneously and thus realizes secure biometric authentication.

(2.3. Imaging Element 120 According to First Embodiment)

Figure 4:
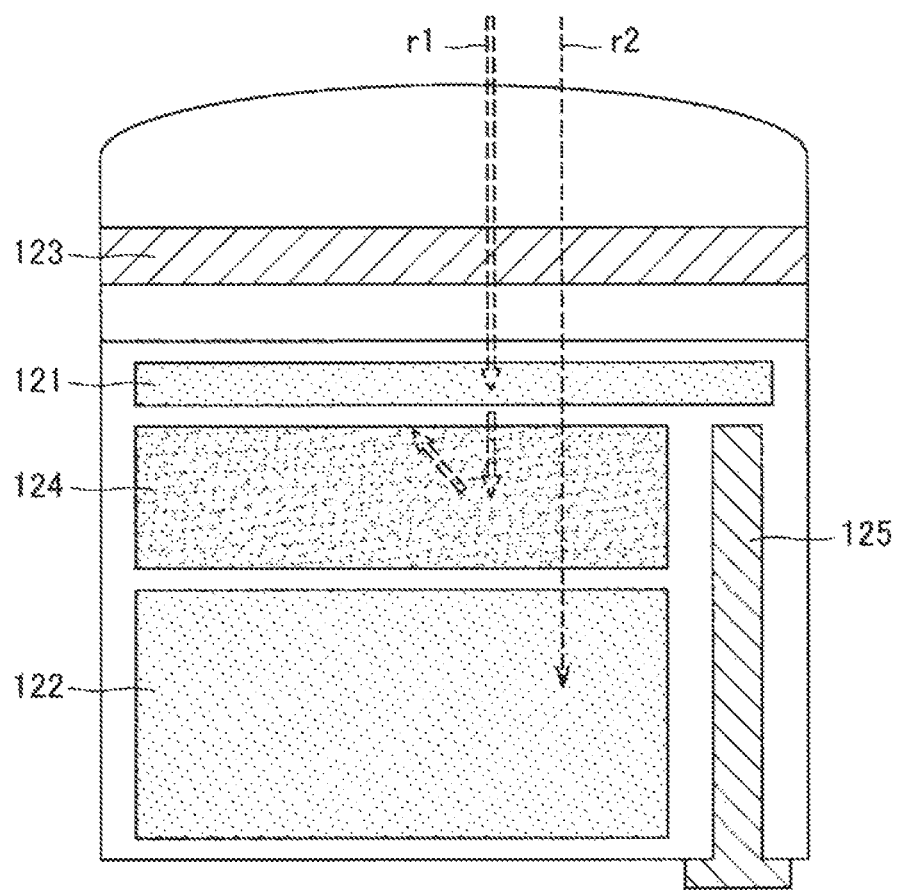
FIG. 4 is a view illustrating the structure of an imaging element according to this embodiment.

Next, the imaging element 120 according to the first embodiment of the present disclosure will be described in detail. As described above, the imaging element 120 according to this embodiment has a function of acquiring signals individually from the light in the first wavelength band and the light in the second wavelength band. Hereinafter, the structure of the imaging element 120 for realizing this function will be described in detail. FIG. 4 is a view illustrating the structure of the imaging element 120 according to this embodiment.

Referring to FIG. 4, the imaging element 120 according to this embodiment includes a first photoelectric conversion unit 121, a second photoelectric conversion unit 122, a color filter 123, a dielectric multilayer film 124, and a vertical gate (VG) 125.

Here, the first photoelectric conversion unit 121 has a function of converting the light r1 in the first wavelength band into an electrical signal. The first photoelectric conversion unit 121 according to this embodiment may be realized by, for example, a photo diode (PD) sensitive to blue to green light from 400 to 580 nm. In other words, the first photoelectric conversion unit 121 according to this embodiment can capture the dermatoglyphic pattern by converting the light r1 in the first wavelength band reflected off the authentication target object into an electrical signal.

In addition, the second photoelectric conversion unit 122 has a function of converting the light r2 in the second wavelength band into an electrical signal. The second photoelectric conversion unit 122 according to this embodiment may be realized by, for example, a photo diode (PD) sensitive to light of 650 nm or more mainly including near-infrared light. In other words, the second photoelectric conversion unit 122 according to this embodiment can capture the vein pattern by converting the light r2 in the second wavelength band reflected off the authentication target object into an electrical signal.

In addition, the imaging element 120 according to this embodiment may include a color filter 123 above the first photoelectric conversion unit 121. For example, a B-on chip color filter (OCCF), a B-G-OCCF, or a G-OCCF may be used as the color filter 123 according to this embodiment. The color filter 123 according to this embodiment can transmit only blue to green light from 400 to 580 nm and light of 650 nm or more mainly including near-infrared light and thus makes it possible to obtain high resolution images.

Furthermore, the imaging element 120 according to this embodiment may include a dielectric multilayer film 124. Here, the dielectric multilayer film 124 according to this embodiment reflects blue to green light from 400 to 580 nm and transmits light of 650 nm or more mainly including near-infrared light. In addition, as illustrated in FIG. 4, the dielectric multilayer film 124 according to this embodiment is disposed between the first photoelectric conversion unit 121 and the second photoelectric conversion unit 122. The dielectric multilayer film 124 according to this embodiment disposed as described above can reflect the light r1 in the first wavelength band that has passed through the first photoelectric conversion unit 121 and can thus enhance the sensitivity of the first photoelectric conversion unit 121.

Furthermore, the imaging element 120 according to this embodiment includes a VG 125 as illustrated in FIG. 4. Accordingly, the signal from the first photoelectric conversion unit 121 according to this embodiment can be read out at the VG 125. In addition, although not illustrated in FIG. 4, the imaging element 120 according to this embodiment may further include a VG 125 for the second photoelectric conversion unit 122. In this case, the signal from the second photoelectric conversion unit 122 according to this embodiment can be read out through floating diffusion (FD).

The structure of the imaging element 120 according to this embodiment is described above in detail. As illustrated in FIG. 4, the imaging element 120 according to this embodiment includes the first photoelectric conversion unit 121 and the second photoelectric conversion unit 122.

In addition, as illustrated in FIG. 4, the first photoelectric conversion unit 121 and the second photoelectric conversion unit 122 according to this embodiment are disposed so as to be stacked in the direction perpendicular to the imaging surface in the bulk. In addition, in this case, the second photoelectric conversion unit 122 is disposed below the first photoelectric conversion unit. The imaging element 120 according to this embodiment can disperse the light r1 in the first wavelength band and the light r2 in the second wavelength band in the direction perpendicular to the imaging surface, and can capture the dermatoglyphic pattern and the vein pattern simultaneously.

3. Second Embodiment (3.1. Light Source 110 According to Second Embodiment)

Next, a second embodiment of the present disclosure will be described. The foregoing description of the first embodiment illustrates the case where the light emitting unit 111 in the light source 110 includes the light emitting element 113, which emits light in the first wavelength band, and the light emitting substance 116, which emits light in the second wavelength band upon being excited by light emitted from the light emitting element. However, the light source 110 according to the second embodiment of the present disclosure includes a light emitting unit 111a, which emits light in the first wavelength band, and a light emitting unit 111b, which emits light in the second wavelength band.

The structure of the light source 110 according to this embodiment will be described in detail. Note that the following description of this embodiment mainly focuses on differences between the first embodiment and the second embodiment. The detailed description of the components and functions common to the first embodiment and the second embodiment is omitted.

Figure 5:
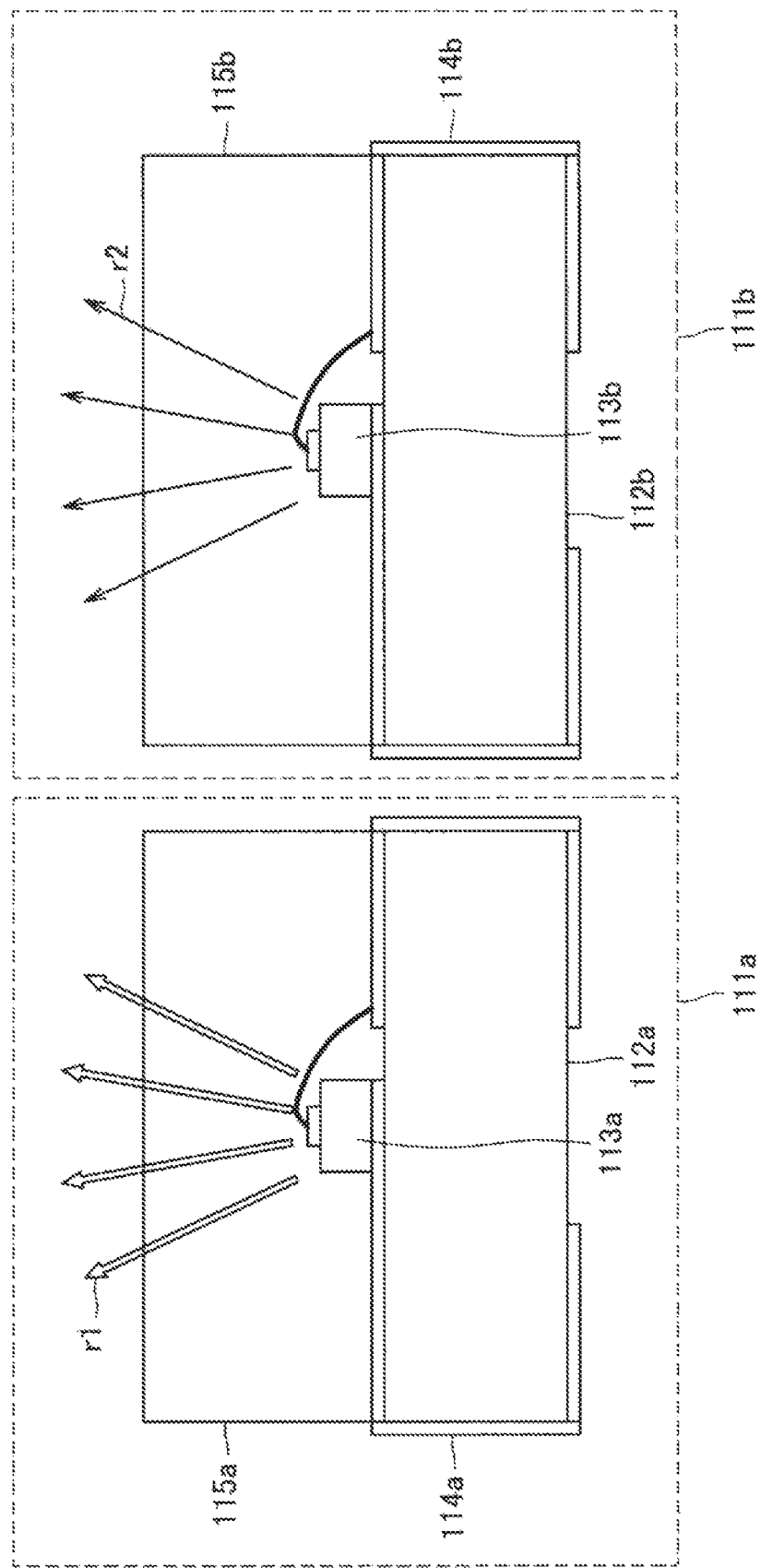
FIG. 5 is a view illustrating the structure of a light emitting unit according to a second embodiment of the present disclosure.

FIG. 5 is a view illustrating the structures of two light emitting units 111a and 111b in the light source 110 according to this embodiment. Here, the light emitting unit 111a according to this embodiment has a function of radiating the light r1 in the first wavelength band from 400 to 580 nm. The light emitting unit 111a according to this embodiment has a function of radiating the light r2 in the second wavelength band of 650 nm or more mainly including near-infrared rays.

Referring to FIG. 5, the light emitting unit 111a according to this embodiment includes a substrate 112a, a light emitting element 113a, an electrode 114a, and a transparent material 115a. Here, these components may be substantially the same as those in the light emitting unit 111 according to the first embodiment described with reference to FIG. 3, and the description thereof is omitted.

Meanwhile, the light emitting unit 111b according to this embodiment includes a substrate 112b, a light emitting element 113b, an electrode 114b, and a transparent material 115b. Similarly, the substrate 112b, the electrode 114b, and the transparent material 115b may be substantially the same as those in the light emitting unit 111 according to the first embodiment described with reference to FIG. 3, and the description thereof is omitted.

Here, the light emitting element 113b according to this embodiment may be realized by an LED, EL, or the like that radiates the light r2 in the second wavelength band of 650 nm or more. For example, a material, such as a GaAs-based material or an InGaAs-based material, may be used for the light emitting element 113b according to this embodiment.

As described above, the light source 110 according to this embodiment includes the light emitting unit 111a, which radiates the light r1 in the first wavelength band, and the light emitting unit 111b, which radiates the light r2 in the second wavelength band. Therefore, the light source 110 according to this embodiment can radiate the light r1 in the first wavelength band and the light r2 in the second wavelength band simultaneously or with a time lag.

In particular, in the case where the light source 110 according to this embodiment radiates the light r1 in the first wavelength band and the light r2 in the second wavelength band with a time lag, the imaging element 120 according to this embodiment does not necessarily have the spectroscopic function as described in the first embodiment. Therefore, the imaging element 120 according to this embodiment may have a structure without a color filter or a dielectric multilayer film, and may capture black-and-white images on which only differences in brightness of light are recorded. In other words, the imaging element 120 according to this embodiment may be a simple monochrome CMOS image sensor (CIS). In this case, the costs for fabricating the imaging device 10 can be greatly reduced.

Furthermore, the radiation of the light r1 in the first wavelength band and the light r2 in the second wavelength band from the light source 110 with a time lag may provide the effect of increasing the number of effective pixels to improve the resolution of the captured image.

4. Third Embodiment (4.1. Imaging Element 120 According to Third Embodiment)

Next, a third embodiment of the present disclosure will be described. The foregoing description of the first embodiment illustrates the case where the imaging element 120 disperses the light r1 in the first wavelength band and the light r2 in the second wavelength band in the direction perpendicular to the imaging surface in the bulk. However, an imaging element 120 according to the third embodiment of the present disclosure includes a plurality of substrates. In this case, the first photoelectric conversion unit 121 and the second photoelectric conversion unit 122 may be disposed on different substrates.

The structure of the imaging element 120 according to this embodiment will be described below in detail. Note that the following description of this embodiment mainly focuses on differences between the third embodiment and the first embodiment. The detailed description of the components and functions common to the third embodiment and the first embodiment is omitted.

Figure 6:
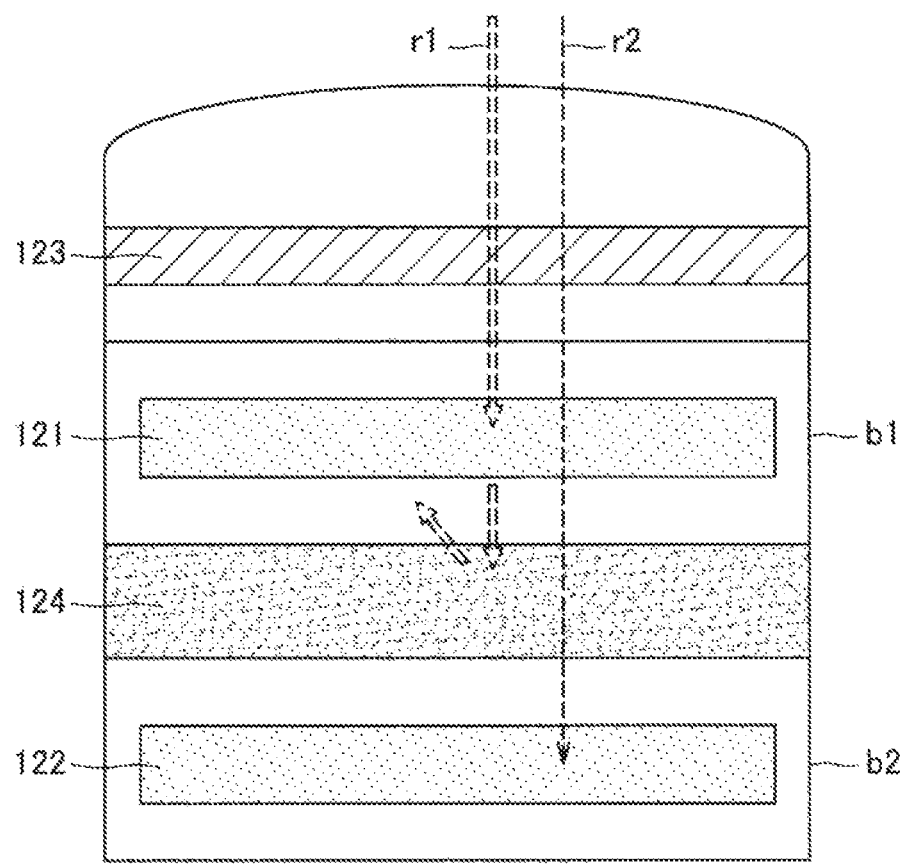
FIG. 6 is a view illustrating the structure of an imaging element according to a third embodiment of the present disclosure.

FIG. 6 is a view illustrating the structure of the imaging element 120 according to this embodiment. Referring to FIG. 6, the imaging element 120 according to this embodiment includes a first photoelectric conversion unit 121, a second photoelectric conversion unit 122, a color filter 123, and a dielectric multilayer film 124.

In this case, the first photoelectric conversion unit 121 and the second photoelectric conversion unit 122 according to this embodiment may be disposed on different substrates. As illustrated in FIG. 6, the first photoelectric conversion unit 121 according to this embodiment is disposed on the substrate b1, and the second photoelectric conversion unit 122 is disposed on the substrate b2. Thus, the imaging element 120 according to this embodiment may be formed by attaching the substrate b1 having the first photoelectric conversion unit 121 to the substrate b2 having the second photoelectric conversion unit 122.

In addition, as illustrated in FIG. 6, the dielectric multilayer film 124 may be disposed between the substrate b1 and the substrate b2 in this case. The dielectric multilayer film 124 disposed at this position can reflect the light r1 in the first wavelength band that has passed through the first photoelectric conversion unit 121 and can thus improve the sensitivity of the first photoelectric conversion unit 121. In addition, as in the first embodiment, the dielectric multilayer film 124 according to this embodiment transmits the light r2 in the second wavelength band. In addition, although not illustrated in FIG. 6, the imaging element 120 according to this embodiment may include a VG 125, as in the first embodiment.

The structure of the imaging element 120 according to this embodiment is described above. As described with reference to FIG. 6, the imaging element 120 according to this embodiment may be formed by attaching the substrate b1 having the first photoelectric conversion unit 121 to the substrate b2 having the second photoelectric conversion unit 122 such that the substrate b1 and the substrate b2 are arranged in the direction perpendicular to the imaging surface. In other words, the first photoelectric conversion unit 121 and the second photoelectric conversion unit 122 according to this embodiment are said to be stacked in the direction perpendicular to the imaging surface.

The imaging element 120 according to this embodiment can disperse the light r1 in the first wavelength band and the light r2 in the second wavelength band in the direction perpendicular to the imaging surface, and can capture the dermatoglyphic pattern and the vein pattern simultaneously or with a time lag.

Here, the imaging element 120 according to this embodiment can also be realized in combination with the light source 110 according to the second embodiment.

5. Fourth Embodiment (5.1. Imaging Element 120 According to Fourth Embodiment)

Next, a fourth embodiment of the present disclosure will be described. The foregoing description of the first and third embodiments illustrates the case where the first photoelectric conversion unit 121 in the imaging element 120 is realized by a PD sensitive to blue to green light from 400 to 580 nm. Here, a first photoelectric conversion unit 121 according to the fourth embodiment of the present disclosure is realized by an organic photoelectric conversion film.

The structure of the imaging element 120 according to this embodiment will be described below in detail. Note that the following description of this embodiment mainly focuses on differences between the fourth embodiment and the first and third embodiments. The detailed description of the components and functions common to the fourth embodiment and the first and third embodiments is omitted.

Figure 7:
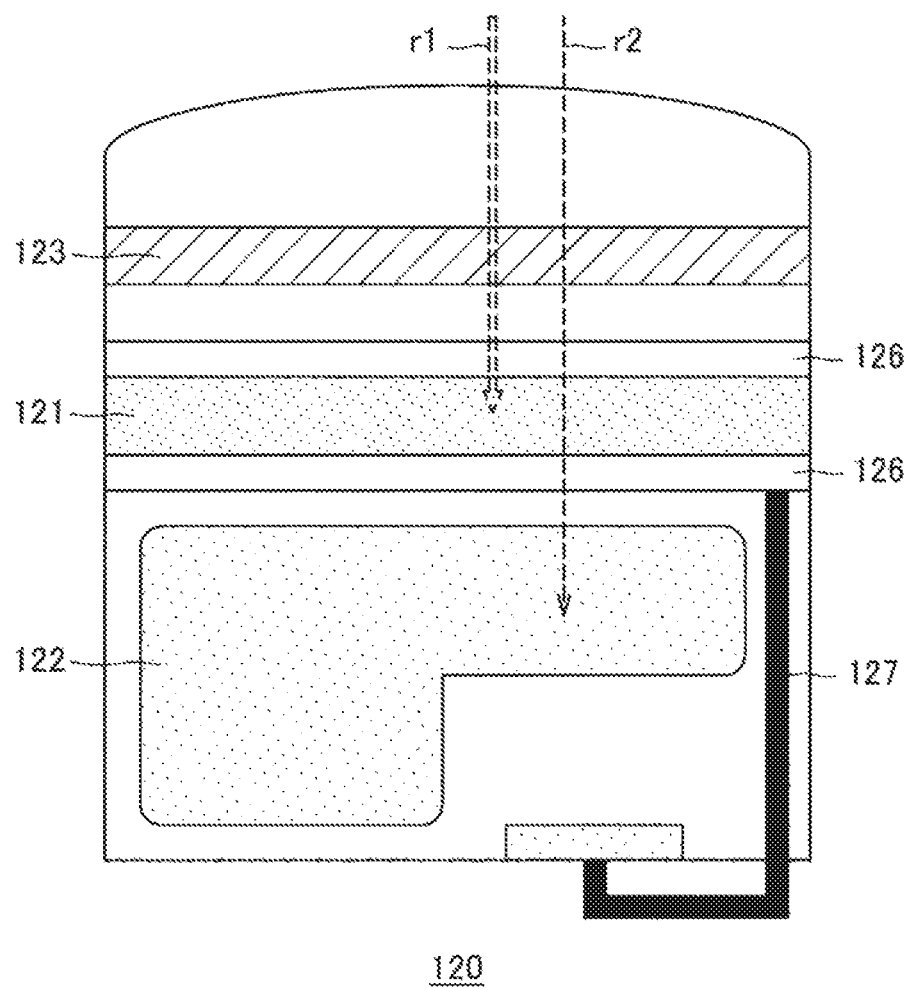
FIG. 7 is a view illustrating the structure of an imaging element according to a fourth embodiment of the present disclosure.

FIG. 7 is a view illustrating the structure of the imaging element 120 according to this embodiment. Referring to FIG. 7, the imaging element 120 according to this embodiment includes a first photoelectric conversion unit 121, a second photoelectric conversion unit 122, a color filter 123, a transparent electrode layer 126, and a plug 127.

As described above, the first photoelectric conversion unit 121 according to this embodiment is realized by an organic photoelectric conversion film sensitive to blue to green light from 400 to 580 nm. In this case, for example, a material, such as fullerene, sensitive to blue to green light from 400 to 580 nm, may be used for the first photoelectric conversion unit 121 according to this embodiment.

In addition, as illustrated in FIG. 7, the imaging element 120 according to this embodiment includes the plug 127 and the transparent electrode layer 126, which is disposed adjacent to the first photoelectric conversion unit 121. According to the above-described structure, the signal from the first photoelectric conversion unit 121 can be read out through the transparent electrode layer 126 and the plug 127. Here, for example, a material, such as indium tin oxide (ITO), may be used for the transparent electrode layer 126 according to this embodiment.

In addition, although not illustrated in FIG. 7, a dielectric multilayer film 124 may be disposed between the first photoelectric conversion unit 121 and the second photoelectric conversion unit 122 according to this embodiment, as in the first and third embodiments. Furthermore, although not illustrated in FIG. 7, the imaging element 120 according to this embodiment may include a VG 125, as in the first embodiment.

The structure of the imaging element 120 according to this embodiment is described above. As described with reference to FIG. 7, the first photoelectric conversion unit 121 according to this embodiment is realized by an organic photoelectric conversion film. Moreover, the first photoelectric conversion unit 121 and the second photoelectric conversion unit 122 according to this embodiment are disposed so as to be stacked in the direction perpendicular to the imaging surface.

The imaging element 120 according to this embodiment can disperse the light r1 in the first wavelength band and the light r2 in the second wavelength band in the direction perpendicular to the imaging surface, and can capture the dermatoglyphic pattern and the vein pattern simultaneously or with a time lag.

Here, the imaging element 120 according to this embodiment can also be realized in combination with the light source 110 according to the second embodiment.

6. Fifth Embodiment (6.1. Imaging Element 120 According to Fifth Embodiment)

Next, a fifth embodiment of the present disclosure will be described. The foregoing description of the first, third, and fourth embodiments illustrates the case where the imaging element 120 disperses the light r1 in the first wavelength band and the light r2 in the second wavelength band in the direction perpendicular to the imaging surface. However, the imaging element according to the fifth embodiment of the present disclosure disperses the light r1 in the first wavelength band and the light r2 in the second wavelength band in the direction horizontal to the imaging surface.

The structure of the imaging element 120 according to this embodiment will be described below in detail. Note that the following description of this embodiment mainly focuses on differences between the fifth embodiment and the first, third, and fourth embodiments. The detailed description of the components and functions common to the fifth embodiment and the first, third, and fourth embodiments is omitted.

Figure 8:
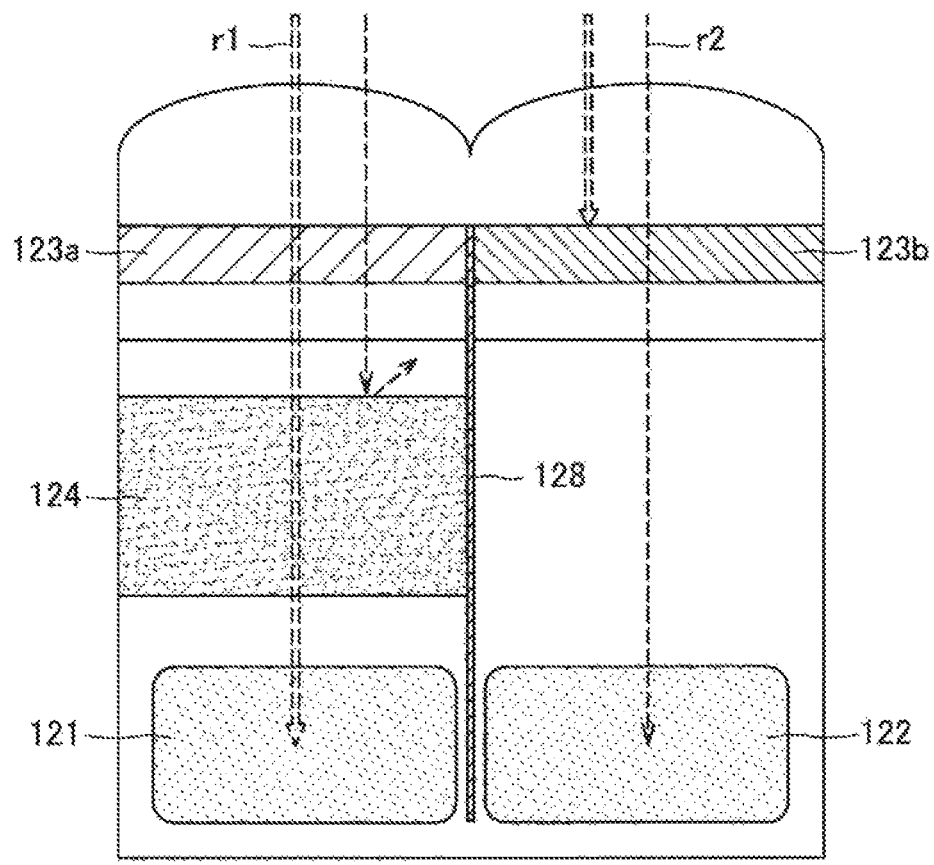
FIG. 8 is a view illustrating the structure of an imaging element according to a fifth embodiment of the present disclosure.

FIG. 8 is a view illustrating the structure of the imaging element 120 according to this embodiment. Referring to FIG. 8, the imaging element 120 according to this embodiment includes a first photoelectric conversion unit 121, a second photoelectric conversion unit 122, color filters 123a and 123b, a dielectric multilayer film 124, and a light shielding wall 128.

As described above, the imaging element 120 according to this embodiment disperses the light r1 in the first wavelength band and the light r2 in the second wavelength band in the direction horizontal to the imaging surface. Thus, the first photoelectric conversion unit 121 and the second photoelectric conversion unit 122 according to this embodiment may be arranged in the direction horizontal to the imaging surface, as illustrated in FIG. 8.

In addition, unlike the first, third, and fourth embodiments, the imaging element 120 according to this embodiment includes two color filters 123a and 123b. In this case, the color filter 123a according to this embodiment is disposed above the first photoelectric conversion unit 121, while the color filter 123b is disposed above the second photoelectric conversion unit 122.

Moreover, the color filter 123a may be realized by a B-OCCF, a B-G-OCCF, or a G-OCCF, as in the first, third, and fourth embodiments. However, the color filter 123b according to this embodiment may be realized by a black (Bk)-OCCF.

Figure 9:
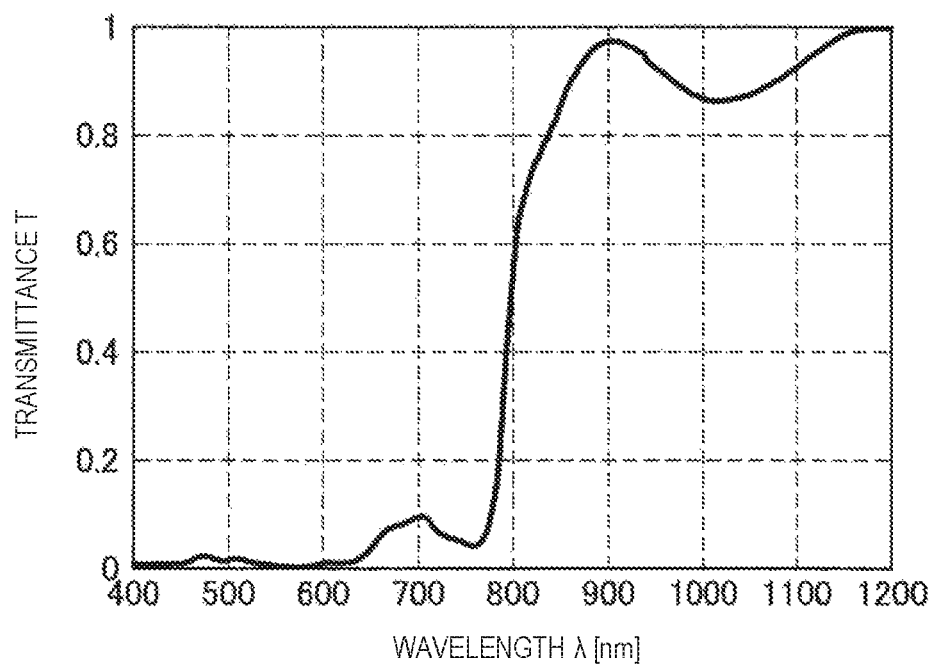
FIG. 9 is a figure illustrating the relationship between transmittance T and wavelength for a Bk-OCCF according to this embodiment.

Here, the Bk-OCCF according to this embodiment may be an OCCF that shields visible light including blue to green light from 400 to 580 nm and transmits light of 650 nm or more mainly including near-infrared light. FIG. 9 is a figure illustrating the relationship between transmittance T and wavelength for the Bk-OCCF according to this embodiment. FIG. 9 indicates that the Bk-OCCF according to this embodiment substantially shields light having a wavelength of less than 650 nm. Meanwhile, the transmittance T of the Bk-OCCF according to this embodiment is over 0.5 at a wavelength of 800 nm or more; and the transmittance T is generally 0.9 or more at a wavelength of 850 nm or more.

In the imaging element 120 according to this embodiment, the color filter 123b including the Bk-OCCF, which is disposed above the second photoelectric conversion unit 122, can selectively transmit the light r2 in the second wavelength band.

In addition, the dielectric multilayer film 124 according to this embodiment is disposed between the color filter 123a and the first photoelectric conversion unit 121. In this case, the dielectric multilayer film 124 according to this embodiment may have transmission spectral characteristics so as to transmit the light r1 in the first wavelength band and reflect the light r2 in the second wavelength band. The dielectric multilayer film 124 according to this embodiment having the above-described characteristics can reflect the light r2 in the second wavelength band that has passed through the color filter 123a before the light r2 reaches the first photoelectric conversion unit 121.

The dielectric multilayer film 124 according to this embodiment may have, for example, the structure shown in Table 1 below.

TABLE 1

| Type of film | Thickness (nm) | Number of layers |
|---|---|---|
| $TiO_2$ | 76.2 | 8 |
| $SiO_2$ | 138.1 | 7 |
| $TiO_2$ | 91.5 | 1 |
| $SiO_2$ | 165.7 | 1 |
| SiN | 80.2 | 1 |
| $HfO_2$ | 67.7 | 1 |
| $SiO_2$ | 85.9 | 1 |

Figure 10:
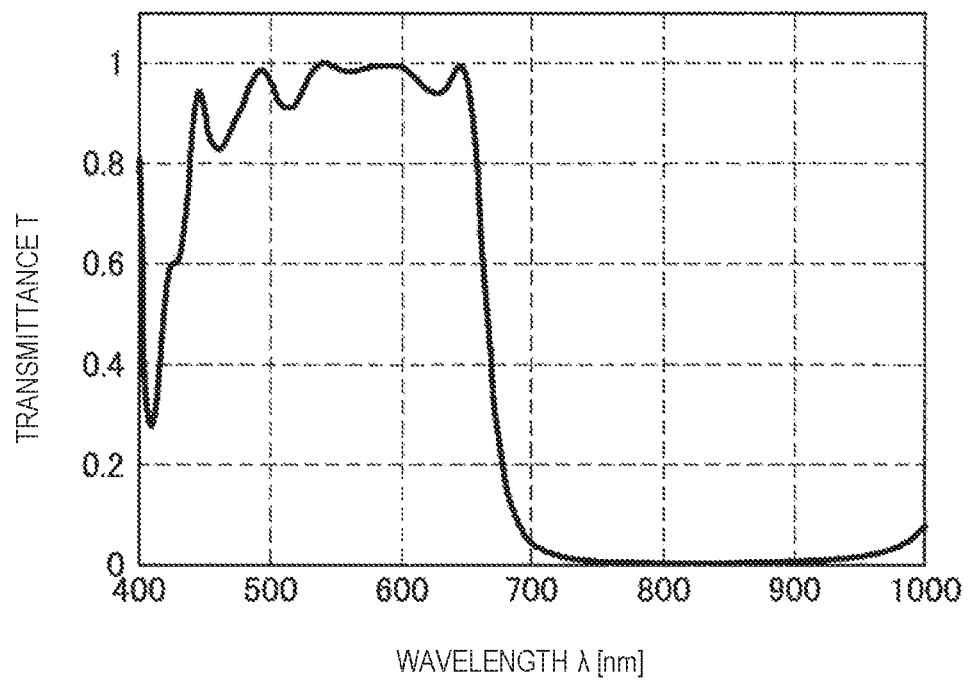
FIG. 10 is a figure illustrating the relationship between transmittance T and wavelength for a dielectric multilayer film according to this embodiment.

FIG. 10 is a figure illustrating the relationship between transmittance T and wavelength for the dielectric multilayer film 124 having the structure shown in Table 1 above. FIG. 10 indicates that the transmittance T of the dielectric multilayer film 124 according to this embodiment for the light r1 in the first wavelength band from 400 to 580 nm is generally over 0.8. Meanwhile, the transmittance T sharply decreases as the wavelength exceeds 650 nm; and the transmittance T is substantially 0 when the wavelength is 750 nm or more.

Accordingly, the dielectric multilayer film 124 according to this embodiment can effectively block the light r2 in the second wavelength band.

Furthermore, as illustrated in FIG. 8, the imaging element 120 according to this embodiment may include a light shielding wall 128. In the case where the light shielding wall 128 according to this embodiment is disposed so as to separate the first photoelectric conversion unit 121 and the second photoelectric conversion unit 122, the light shielding wall 128 can prevent the light r1 in the first wavelength band and the light r2 in the second wavelength band from being mixed with each other and can thus maintain the resolution of the captured image high.

The structure of the imaging element 120 according to this embodiment is described above. As described with reference to FIG. 8, the first photoelectric conversion unit 121 and the second photoelectric conversion unit 122 according to this embodiment are arranged in the direction horizontal to the imaging surface.

The imaging element 120 according to this embodiment can disperse the light r1 in the first wavelength band and the light r2 in the second wavelength band in the horizontal direction, and can capture the dermatoglyphic pattern and the vein pattern simultaneously or with a time lag.

7. Sixth Embodiment (7.1. Proximity Imaging Device 10 According to Sixth Embodiment)

Figure 11:
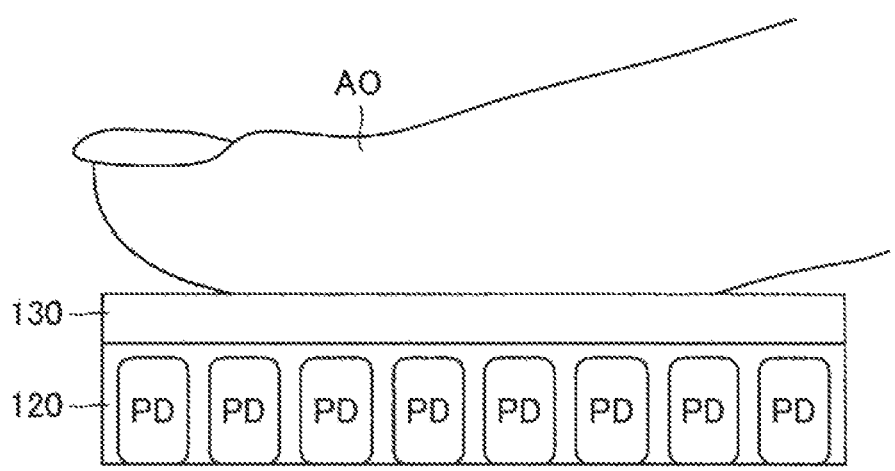
FIG. 11 is a view for describing a proximity imaging device according to a sixth embodiment of the present disclosure.

Next, a sixth embodiment of the present disclosure will be described. An imaging device 10 according to the sixth embodiment of the present disclosure may be a proximity imaging device including the light source 110 and the imaging element 120 described in the first to fifth embodiments. FIG. 11 is a view for describing a proximity imaging device 10 according to this embodiment.

Referring to FIG. 11, the proximity imaging device 10 according to this embodiment further includes a transparent substrate 130 in addition to the light source 110 (not illustrated) and the imaging element 120 described in the first to fifth embodiments.

The transparent substrate 130 according to this embodiment is disposed between the imaging element 120 and an authentication target object AO. The transparent substrate 130 according to this embodiment may be made of, for example, glass, transparent resin, or the like. As illustrated in FIG. 11, the proximity imaging device 10 according to this embodiment can capture the dermatoglyphic pattern and the vein pattern simultaneously or with a time lag when the authentication target object AO is placed directly on the upper surface of the transparent substrate 130. Note that, although the light source 110 is not illustrated in FIG. 11 and the subsequent figures, the light source 110 is actually disposed on the same side as the imaging element 120 with respect to the authentication target object AO. In other words, the light source 110 radiates the light r1 in the first wavelength band and the light r2 in the second wavelength band toward the authentication target object AO in the direction horizontal to the imaging element 120.

Here, FIG. 11 simply illustrates the structure of the imaging element 120. In the example illustrated in FIG. 11, the imaging element 120 includes a plurality of photo diodes (PDs) inside. The plurality of PDs may each correspond to the first photoelectric conversion unit 121 or the second photoelectric conversion unit 122 described in the first and third to fifth embodiments. In other words, the detailed structure of the imaging element 120 according to this embodiment accords with the structure of any one of the imaging elements 120 described in the first and third to fifth embodiments.

Furthermore, in the case where the proximity imaging device 10 according to this embodiment includes two light emitting units 111a and 111b as described in the second embodiment, the imaging element according to this embodiment may be a monochrome CIS with no color filter.

Figure 12:
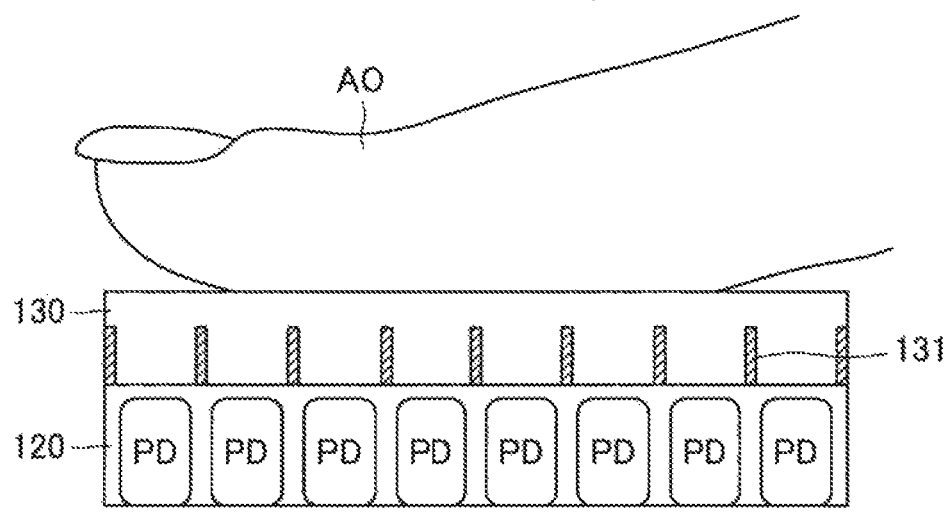
FIG. 12 is a view for describing a light shielding substrate including a light shielding film according to this embodiment.

In addition, in the proximity imaging device 10 according to this embodiment, the transparent substrate 130 may include a light shielding film 131. FIG. 12 is a view for describing the imaging device 10 in which the transparent substrate 130 according to this embodiment includes light shielding films 131.

As illustrated in FIG. 12, the transparent substrate 130 according to this embodiment includes a plurality of light shielding films 131, and the light shielding films 131 are disposed in the direction perpendicular to the imaging surface of the imaging element 120. The light shielding films 131 as illustrated in FIG. 12 in the transparent substrate 130 according to this embodiment are expected to have the effects of shielding stray light coming from the surroundings and maintaining the resolution of the captured image high.

8. Seventh Embodiment (8.1. Image Forming Lens-Type Imaging Device 10 According to Seventh Embodiment)

Next, a seventh embodiment of the present disclosure will be described. An imaging device 10 according to the seventh embodiment of the present disclosure may be an image forming lens-type imaging device including the light source 110 and the imaging element 120 described in the first to fifth embodiments. In other words, unlike the proximity imaging device 10 described in the sixth embodiment, the image forming lens-type imaging device 10 according to this embodiment may include a light collecting mechanism that collects the light r1 in the first wavelength band and the light r2 in the second wavelength band onto the imaging element 120. The light collecting mechanism according to this embodiment may be, for example, a pinhole and an image forming lens.

Note that the following description of this embodiment mainly focuses on differences between the seventh embodiment and the sixth embodiment. The detailed description of the components and effects common to the seventh embodiment and the sixth embodiment is omitted.

Figure 13:
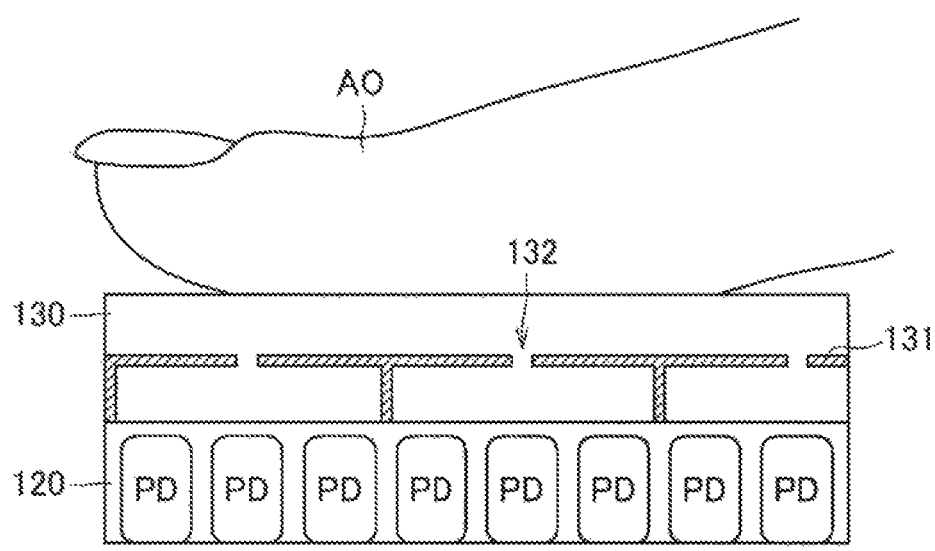
FIG. 13 is a view for describing an imaging device including a pinhole according to a seventh embodiment of the present disclosure.

FIG. 13 is a view for describing an imaging device 10 having pinholes according to this embodiment. Referring to FIG. 13, the imaging device 10 having pinholes according to this embodiment includes a light source 110 (not illustrated), an imaging element 120, and a transparent substrate 130.

Here, the transparent substrate 130 according to this embodiment may include light shielding films 131 as in the case illustrated in FIG. 12. However, the light shielding films 131 according to this embodiment include those disposed in the direction horizontal to the imaging surface, and the light shielding films 131 disposed in the horizontal direction have at least one or more pinholes 132.

Furthermore, as illustrated in FIG. 13, at least one or more pinholes 132 may be formed for a plurality of PDs in the imaging device 10 according to this embodiment. The pinhole 132 according to this embodiment formed as described above enables the light r1 in the first wavelength band and the light r2 in the second wavelength band to be effectively collected onto the imaging element 120.

Figure 14:
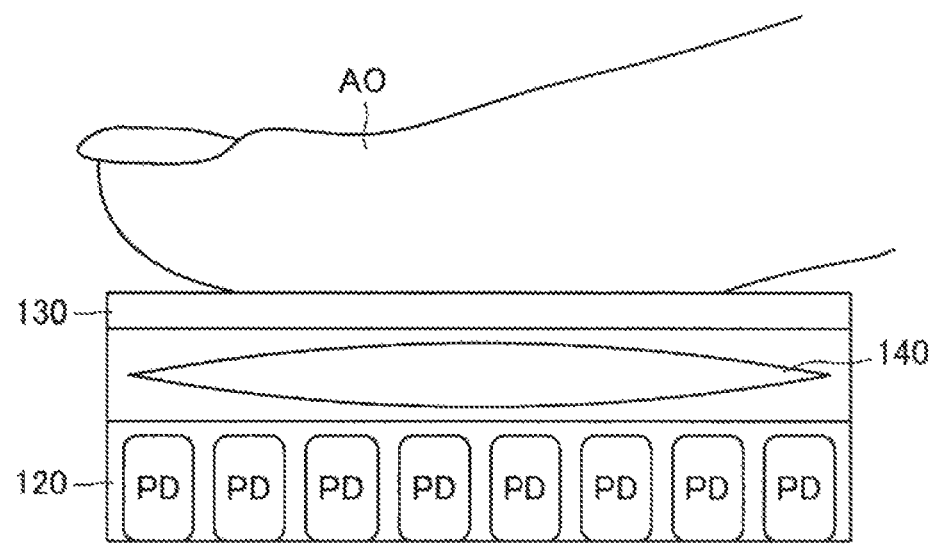
FIG. 14 is a view for describing an imaging device including a single image forming lens according to this embodiment.

Next, an imaging device 10 having a single image forming lens according to this embodiment will be described. Referring to FIG. 14, the imaging device 10 having a single image forming lens according to this embodiment includes a light source 110 (not illustrated), an imaging element 120, a transparent substrate 130, and a single image forming lens 140.

Here, the image forming lens 140 according to this embodiment is disposed between the imaging element 120 and the transparent substrate 130, as illustrated in FIG. 14. The single image forming lens 140 thus provided in the imaging device 10 enables the light r1 in the first wavelength band and the light r2 in the second wavelength band to be effectively collected onto the imaging element 120 under the same optical conditions. As a result, the effect of improving the resolution of the captured image is expected.

Figure 15:
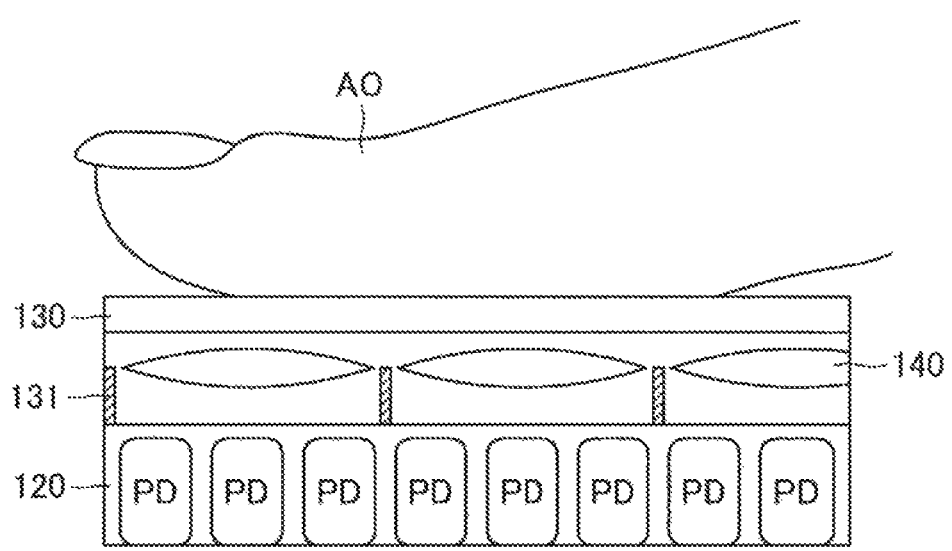
FIG. 15 is a view for describing an imaging device including a plurality of image forming lenses according to this embodiment.

Alternatively, the imaging device 10 according to this embodiment may include a plurality of image forming lenses 140. FIG. 15 is a view for describing an imaging device 10 including a plurality of image forming lenses 140 according to this embodiment.

Referring to FIG. 15, the imaging device 10 having a plurality of image forming lens 140 according to this embodiment includes a light source 110 (not illustrated), an imaging element 120, a transparent substrate 130, and a plurality of image forming lenses 140.

Here, the plurality of image forming lenses 140 is disposed between the imaging element 120 and the transparent substrate 130, as in the example illustrated in FIG. 14. Furthermore, as illustrated in FIG. 15, at least one or more image forming lenses 140 may be formed for a plurality of PDs in the imaging device 10 according to this embodiment. Moreover, a light shielding film 131 may be disposed between the image forming lenses 140 in this case. This structure shields stray light coming from the surroundings and improves the sensitivity of the PDs and the resolution of the captured image while the image forming lenses 140 have a small thickness. As a result, the imaging device 10 has a small thickness.

In addition, in the case where the imaging device 10 includes an imaging element that disperses light in the horizontal direction as described in the fifth embodiment, the imaging device 10 according to this embodiment may include two types of image forming lenses 140a and 140b, which respectively collect light onto the first photoelectric conversion unit 121 and the second photoelectric conversion unit 122.

Figure 16:
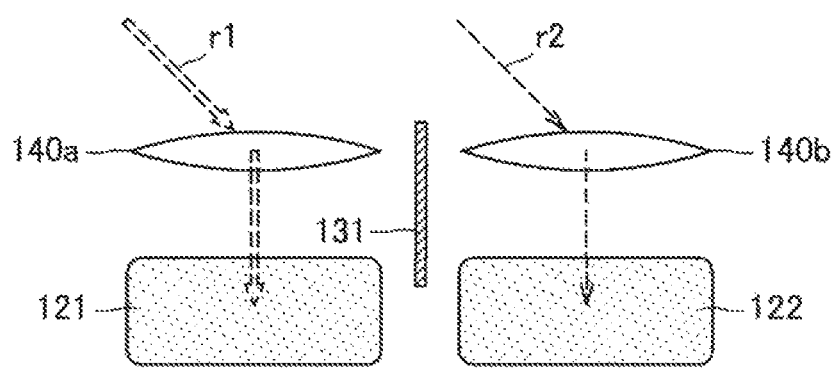
FIG. 16 is a view for describing two types of image forming lenses that collect light on a first photoelectric conversion unit and a second photoelectric conversion unit according to this embodiment.

FIG. 16 is a view for describing two types of image forming lenses 140a and 140b, which respectively collect light onto the first photoelectric conversion unit 121 and the second photoelectric conversion unit 122. Referring to FIG. 16, the imaging device 10 includes the first image forming lens 140a, which collects the light r1 in the first wavelength band onto the first photoelectric conversion unit 121, and the second image forming lens 140b, which collects the light r2 in the second wavelength band onto the second photoelectric conversion unit 122.

Here, the first image forming lens 140a and the second image forming lens 140b may have different optical features. The optical features may change with, for example, the shape or material of the lens, such as thickness. In the case where the first image forming lens 140a and the second image forming lens 140b according to this embodiment have different optical features, a difference between the distance from the first photoelectric conversion unit 121 to the dermatoglyphic pattern and the distance from the second photoelectric conversion unit 122 to the veins is absorbed, which makes it possible to capture a clear image.

9. Conclusion

As described above, the imaging device 10 according to the present disclosure includes the light source 110, which radiates light in two different wavelength bands. The light source 110 has a function of radiating the light r1 in the first wavelength band from 400 to 580 nm for use in dermatoglyphic pattern authentication, and the light r2 in the second wavelength band of 650 nm or more mainly including near-infrared rays for use in vein authentication. In addition, the imaging device 10 according to the present disclosure includes the imaging element 120, which is configured to disperse the light r1 in the first wavelength band and the light r2 in the second wavelength band and acquire signals individually from the light r1 and the light r2. According to this structure, it is possible to acquire a plurality of physical features for use in biometric authentication with a compact housing.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)

An imaging device including:

a light source configured to radiate light in at least two different wavelength bands; and an imaging element configured to acquire signals individually from the light in two different wavelength bands, in which the two different wavelength bands include a first wavelength band from 400 to 580 nm for use in dermatoglyphic pattern authentication, and a second wavelength band of 650 nm or more mainly including near-infrared rays for use in vein authentication.

(2)

The imaging device according to (1), in which the imaging element is configured to acquire a signal from light radiated from the light source and reflected off an authentication target object.

(3)

The imaging device according to (1) or (2), in which the light source and the imaging element are disposed on a same side with respect to an authentication target object.

(4)

The imaging device according to any one of (1) to (3), in which the light source is configured to radiate the light in the first wavelength band and the light in the second wavelength band simultaneously.

(5)

The imaging device according to any one of (1) to (4), in which the light source includes a light emitting element configured to emit the light in the first wavelength band, and a light emitting substance that emits the light in the second wavelength band upon being excited by the light emitted from the light emitting element.

(6)

The imaging device according to any one of (1) to (3), in which the light source is configured to radiate the light in the first wavelength band and the light in the second wavelength band with a time lag.

(7)

The imaging device according to (6), in which the imaging element lacks one or both of a color filter and a dielectric multilayer film.

(8)

The imaging device according to any one of (1) to (5), in which the imaging element includes a first photoelectric conversion unit and a second photoelectric conversion unit, the first photoelectric conversion unit is configured to convert the light in the first wavelength band into an electrical signal, and the second photoelectric conversion unit is configured to convert the light in the second wavelength band into an electrical signal.

(9)

The imaging device according to (8), in which the first photoelectric conversion unit and the second photoelectric conversion unit are stacked in a direction perpendicular to an imaging surface.

(10)

The imaging device according to (8), in which the first photoelectric conversion unit and the second photoelectric conversion unit are arranged in a direction horizontal to an imaging surface.

(11)

The imaging device according to (10), further including:

a first image forming lens that collects light onto the first photoelectric conversion unit; and a second image forming lens that collects light onto the second photoelectric conversion unit, in which the first image forming lens and the second image forming lens have different optical features.

(12)

The imaging device according to any one of (1) to (11), further including a transparent substrate disposed between the imaging element and an authentication target object.

(13)

The imaging device according to (12), in which the transparent substrate includes at least one or more light shielding films, and the light shielding film is disposed in a direction perpendicular to an imaging surface of the imaging element.

(14)

The imaging device according to (13), in which the light shielding film is disposed in a direction horizontal to the imaging surface, and the light shielding film disposed in the horizontal direction has at least one or more pinholes.

(15)

The imaging device according to (12) or (13), further including at least one or more image forming lenses that form an image on the imaging element, in which the image forming lens is disposed between the imaging element and the transparent substrate.

REFERENCE SIGNS LIST 10 imaging device
110 light source
111 light emitting unit
113 light emitting element
116 light emitting substance
120 imaging element
121 first photoelectric conversion unit
122 second photoelectric conversion unit
123 color filter 124 dielectric multilayer film
130 transparent substrate
131 light shielding film
132 pinhole
140 image forming lens
140a first image forming lens
140b second image forming lens

The invention claimed is:

1. An imaging device, comprising:
a light source configured to radiate light in at least two different wavelength bands;
an imaging element configured to acquire signals individually from the light in the at least two different wavelength bands, wherein
the imaging element includes:
a first photoelectric conversion unit,
a second photoelectric conversion unit, and
a dielectric multilayer film between the first photoelectric conversion unit and the second photoelectric conversion unit, and
the at least two different wavelength bands include:
a first wavelength band from 400 nm to 580 nm for use in dermatoglyphic pattern authentication, and
a second wavelength band of 650 nm or more including near-infrared rays for use in vein authentication;
a transparent substrate on the imaging element;
a plurality of image forming lenses between the imaging element and the transparent substrate; and
a light shielding film between a first image forming lens of the plurality of image forming lenses and a second image forming lens of the plurality of image forming lenses.

2. The imaging device according to claim 1, wherein the imaging element is further configured to acquire a signal of the signals from the light radiated from the light source and reflected off an authentication target object.

3. The imaging device according to claim 1, wherein the light source and the imaging element are on a same side with respect to an authentication target object.

4. The imaging device according to claim 1, wherein the light source is further configured to radiate the light in the first wavelength band and the light in the second wavelength band simultaneously.

5. The imaging device according to claim 1, wherein
the light source includes a light emitting element and a light emitting substance,
the light emitting element is configured to:
emit the light in the first wavelength band, and
excite the light emitting substance based on the emission of the light in the first wavelength band, and
the light emitting substance is configured to emit the light in the second wavelength band based on the excitation of the light emitting substance.

6. The imaging device according to claim 1, wherein the light source is further configured to radiate the light in the first wavelength band and the light in the second wavelength band with a time lag.

7. The imaging device according to claim 6, wherein the imaging element lacks a color filter.

8. The imaging device according to claim 1, wherein
the first photoelectric conversion unit is configured to convert the light in the first wavelength band into a first electrical signal, and
the second photoelectric conversion unit is configured to convert the light in the second wavelength band into a second electrical signal.

9. The imaging device according to claim 8, wherein the first photoelectric conversion unit and the second photoelectric conversion unit are in a direction perpendicular to an imaging surface of the imaging element.

10. The imaging device according to claim 1, wherein the transparent substrate is between the imaging element and an authentication target object.

11. The imaging device according to claim 10, wherein
the transparent substrate includes a plurality of light shielding films, and
the plurality of light shielding films is in a direction perpendicular to an imaging surface of the imaging element.

12. The imaging device according to claim 11, wherein
the plurality of light shielding films is in a horizontal direction with respect to the imaging surface, and
the plurality of light shielding films in the horizontal direction includes a plurality of pinholes.

13. The imaging device according to claim 10, wherein the plurality of image forming lenses is configured to form an image on the imaging element.

* * * * *